United States Patent
Reich et al.

(10) Patent No.: US 10,646,723 B2
(45) Date of Patent: May 12, 2020

(54) DEVICE FOR MAGNETIC STIMULATION OF THE VESTIBULAR SYSTEM

(71) Applicant: THE JOHNS HOPKINS UNIVERSITY, Baltimore, MD (US)

(72) Inventors: Daniel H. Reich, Baltimore, MD (US); Collin L. Broholm, Ellicott City, MD (US); David Zee, Ellicott City, MD (US); Dale Roberts, Halethorpe, MD (US); Michael C. Schubert, Parkton, MD (US); Jorge Otero-Millan, Baltimore, MD (US); Bryan Ward, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 135 days.

(21) Appl. No.: 15/668,896

(22) Filed: Aug. 4, 2017

(65) Prior Publication Data
US 2018/0036549 A1 Feb. 8, 2018

Related U.S. Application Data

(60) Provisional application No. 62/370,767, filed on Aug. 4, 2016.

(51) Int. Cl.
*A61N 2/00* (2006.01)
*A61N 2/02* (2006.01)
*G06F 3/01* (2006.01)

(52) U.S. Cl.
CPC .............. *A61N 2/004* (2013.01); *A61N 2/02* (2013.01); *G06F 3/011* (2013.01)

(58) Field of Classification Search
CPC ...................... A61N 2/004; A61N 2/02; A61B 2018/00327; G06F 3/011
See application file for complete search history.

(56) References Cited

U.S. PATENT DOCUMENTS

| | | | | |
|---|---|---|---|---|
| 6,314,324 B1* | 11/2001 | Lattner | .............. | A61N 1/36036 600/26 |
| 2002/0099257 A1* | 7/2002 | Parker | ................... | A61M 21/00 600/27 |
| 2008/0272784 A1* | 11/2008 | Harvey | ................ | G01R 33/385 324/318 |

(Continued)

*Primary Examiner* — Christine H Matthews
*Assistant Examiner* — Joshua Daryl D Lannu
(74) *Attorney, Agent, or Firm* — Johns Hopkins Technology Ventures

(57) ABSTRACT

The present invention is directed to a magnetic vestibular stimulation (MVS) system for rehabilitation of subjects with vestibular and balance disorders. The magnetic vestibular stimulation system includes a magnet and a cooling system. In some embodiments, the subject wears video goggles in order to stimulate the subject to orient to a virtual reality. The subject can lie, sit or stand in or near a strong magnetic field generated by the system. The magnetic field generated by the system stimulates the vestibular system to counteract the inherent imbalance created by a naturally-occurring vestibular disorder. Particularly important, the direction and amplitude of vestibular stimulation can be easily manipulated by altering the orientation and distance of the head relative to the magnetic field vector. Thus, MVS can be precisely tailored to a patient's specific pattern of vestibular disturbance.

16 Claims, 6 Drawing Sheets

(56) References Cited

U.S. PATENT DOCUMENTS

| | | | |
|---|---|---|---|
| 2013/0130914 A1* | 5/2013 | Boffo | G21K 1/093 |
| | | | 505/211 |
| 2013/0137918 A1 | 5/2013 | Phillips et al. | |
| 2013/0150653 A1* | 6/2013 | Borsody | A61N 2/006 |
| | | | 600/13 |
| 2014/0135590 A1* | 5/2014 | Pedro | A61B 5/0205 |
| | | | 600/301 |

\* cited by examiner

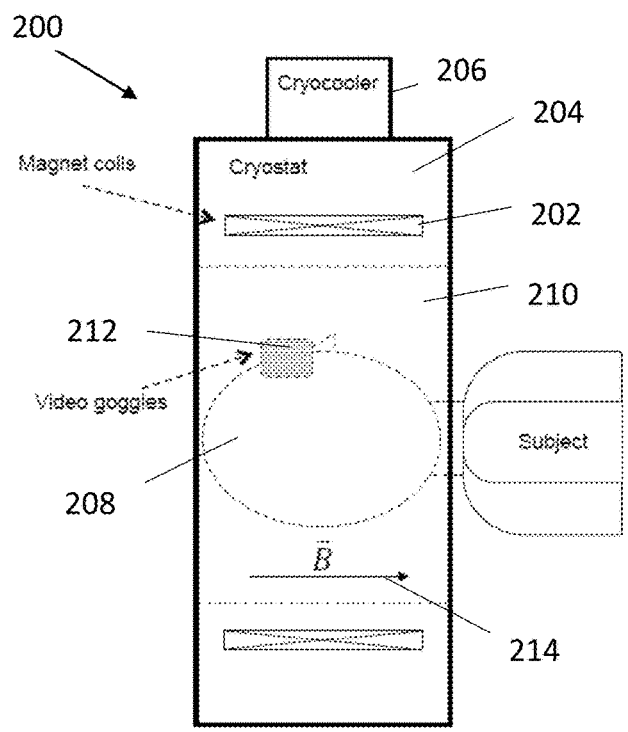
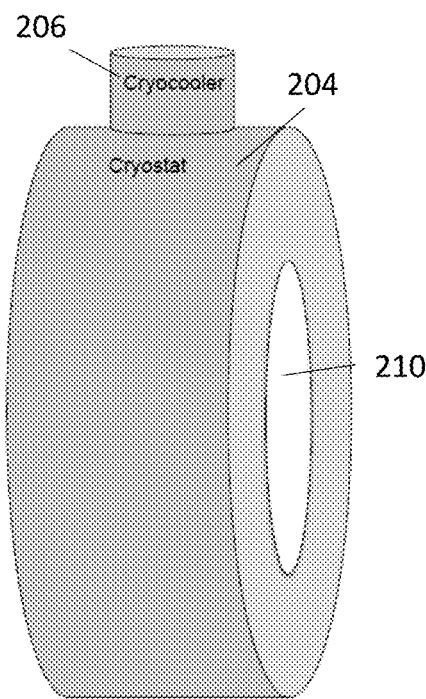
FIG. 3A  FIG. 3B

DEVICE FOR MAGNETIC STIMULATION OF THE VESTIBULAR SYSTEM

CROSS REFERENCE TO RELATED APPLICATIONS

This application claims the benefit of U.S. Provisional Patent Application No. 62/370,767, filed on Aug. 4, 2016, which is incorporated by reference herein, in its entirety.

GOVERNMENT RIGHTS

This invention was made with government support under P41RR015241, R21DC011919-02, and T32DC000027-22 awarded by the National Institutes of Health. The government has certain rights in the invention.

FIELD OF THE INVENTION

The present invention relates generally to a medical device. More particularly, the present invention relates to a device for magnetic stimulation of the vestibular system.

BACKGROUND OF THE INVENTION

Vestibular disorders (dizziness, vertigo, imbalance, coming from both peripheral labyrinthine disorders and central brain disorders) are ubiquitous problems in clinical medicine. They account for staggering numbers (4 million/year) of visits to emergency departments and often produce prolonged physical (and psychological) disability leading to a loss of economic productivity and a high risk of falls and injuries. The treatment of such disorders commonly requires physical therapy (PT) to encourage rebalancing of the vestibular system both with the patient still and when moving. Such patients are prescribed exercises of progressive difficulty which are usually effective when compliance is sustained (unfortunately not often the case). Exercises must be challenging yet performed safely, and be practiced frequently and for many minutes each day. Current approaches are often complex and difficult for patients to perform and/or endure.

It would therefore be advantageous to provide a more practical/flexible device than is currently available for stimulation of the vestibular system.

SUMMARY OF THE INVENTION

The foregoing needs are met by the present invention directed to a system for magnetic stimulation of a vestibular system of a subject including a cooling system. The system also includes a magnet configured to generate a magnetic field directed to and configured for stimulation of the vestibular system.

In accordance with an aspect of the present invention, the system includes a unidirectional magnetic field or a multi-directional magnetic field. The magnetic field can be of a 7T strength. The system includes a computing device for control of the system and its components. The goggles further include video cameras to monitor movements of both eyes and a magnetic field sensor. The goggles also include a video display. The system includes a device for tracking position and posture of the subject. Additionally, the system includes a subject space defined by a housing of the cryostat. The magnet can take the form of a superconducting magnet configured for vestibular stimulation. The cooling system can include a cryostat and a cryocooler.

In accordance with an aspect of the present invention, a method for magnetic stimulation of a vestibular system of a subject includes generating a magnetic field using a source of a magnetic field. The method includes cryocooling the source of the magnetic field. The method also includes directing the magnetic field to the subject and stimulating the vestibular system of the subject using the magnetic field.

In accordance with an aspect of the present invention, the method includes using a unidirectional magnetic field. Alternately, the method includes using a multi-directional magnetic field. The method includes using a magnetic field taking the form of a 7T strength. The method includes using a computing device to implement aspects of the method. The method can also include using goggles that comprise video cameras to monitor movements of both eyes. The goggles can include a magnetic field sensor and in some instances a video display.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 3A illustrates a schematic diagram of a magnetic vestibular stimulation system, according to an embodiment of the present invention.

FIG. 3B illustrates a perspective view of a cylindrical cryostat and cryocooler according to an embodiment of the present invention.

DETAILED DESCRIPTION

Figures 1A, 1B:
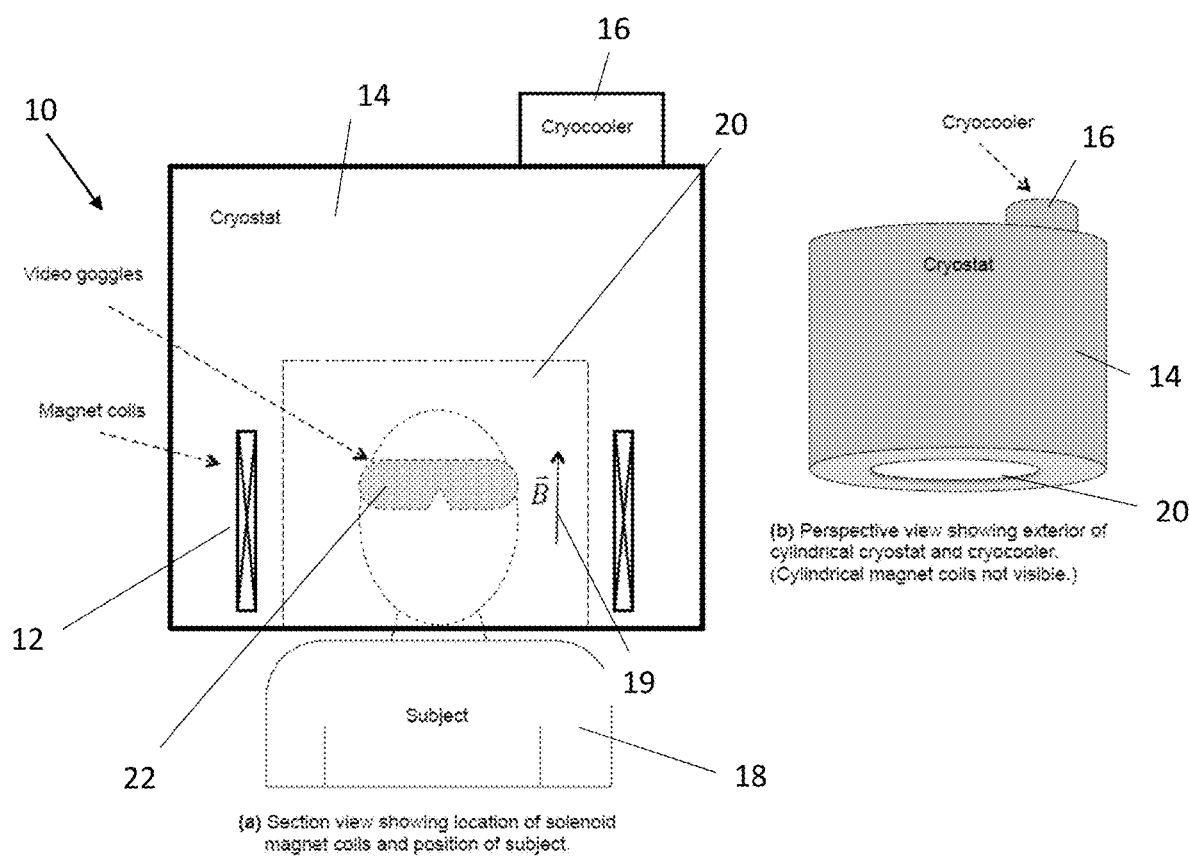
FIG. 1A illustrates a schematic diagram of a magnetic vestibular stimulation system, according to an embodiment of the present invention.
FIG. 1B illustrates a perspective view of a cylindrical cryostat and cryocooler according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a magnetic vestibular stimulation (MVS) system for diagnosis and rehabilitation of subjects with vestibular and balance disorders, and for research and investigational, and entertainment/training purposes. The magnetic vestibular stimulation system includes a system for applying a magnetic field to the vestibular system. The subject wears video goggles in order to present visual stimuli to the subject. The subject can lie, sit or stand in or near a strong magnetic field generated by the system. Particularly important, the direction and amplitude of vestibular stimulation can be easily manipulated by altering the orientation and distance of the head relative to the magnetic field vector. Thus, MVS can be precisely tailored to a patient's specific pattern of vestibular disturbance. The present invention can also be used for diagnosis, research, virtual reality (VR) stimulation, treatment of cognitive disorders and any other use known to or conceivable by one of skill in the art. In some embodiments, a device according to the present invention can be used as a component for flight simulation and/or training for Earth or space travel.

MVS has the ability to produce a sustained peripheral vestibular imbalance, similar to a unilateral vestibular lesion, relatively effortlessly, for hours in humans or experimental animals. This cannot be achieved with other vestibular stimuli and allows one to investigate the multiple timescales of adaptation to a sustained, unwanted vestibular imbalance. Combined with MRI imaging, MVS might reveal the anatomical substrate and changes in default networks that underlie vestibular adaptation. Finally, MVS might be used in rehabilitation in set-point adaptation diseases by inducing a new bias to counteract a pathological one. Examples include not only vestibular dysfunction, but higher-level behavioral disorders such as unilateral visual neglect, which can be ameliorated in response to other types of vestibular stimuli.

FIG. 1A illustrates a schematic diagram of a magnetic vestibular stimulation system, according to an embodiment of the present invention. The magnetic vestibular stimulation system 10 includes a magnet 12, preferably in some embodiments the magnet takes the form of superconducting magnetic coils. The magnet 12 takes the form of a cylinder disposed in a cooling system. The cooling system as illustrated in FIG. 1A takes the form of a cryostat 14 and also includes a cryocooler 16. However, any suitable cooling system known to or conceivable to one of skill in the art can also be used. Further, as illustrated in FIG. 1A, the subject 18 is disposed within a subject space 20 defined by the cryostat 14. The subject 18 wears video goggles 22 in order to provide a virtual reality experience within the magnetic vestibular system, and to record subject eye movements, head and body movements, and magnetic field strength and direction. This provides the subject 18 with the rehabilitation needed for the vestibular or balance disorder being treated or with a virtual reality experience for training, entertainment, or other application. FIG. 1A also illustrates the position of the subject 18 within the subject space 20 of the magnetic vestibular stimulation system 10. The subject 18 is positioned vertical with respect to the cryostat 14. A magnetic field $\vec{B}$ 19 is also oriented vertically, parallel to a vertical axis of the cryostat 14, such that the subject 18 and the magnetic field are oriented in the same direction.

FIG. 1B illustrates a perspective view of a cylindrical cryostat and cryocooler for the magnetic vestibular stimulation system, according to an embodiment of the present invention. As illustrated in FIG. 1B the cryostat 14 takes the form of a cylinder. The cylinder of the cryostat 14 defines subject space 20, which as illustrated in FIG. 1B also takes the form of a cylinder. While cylindrical shapes are shown in FIGS. 1A and 1B, the cryostat 14 and subject space 20 can take any shape known to or conceivable to one of skill in the art. The cryostat 14 also includes a cryocooler 16. The cryostat 14 and cryocooler 16 can take any form known to or conceivable to one of skill in the art.

Figure 2:
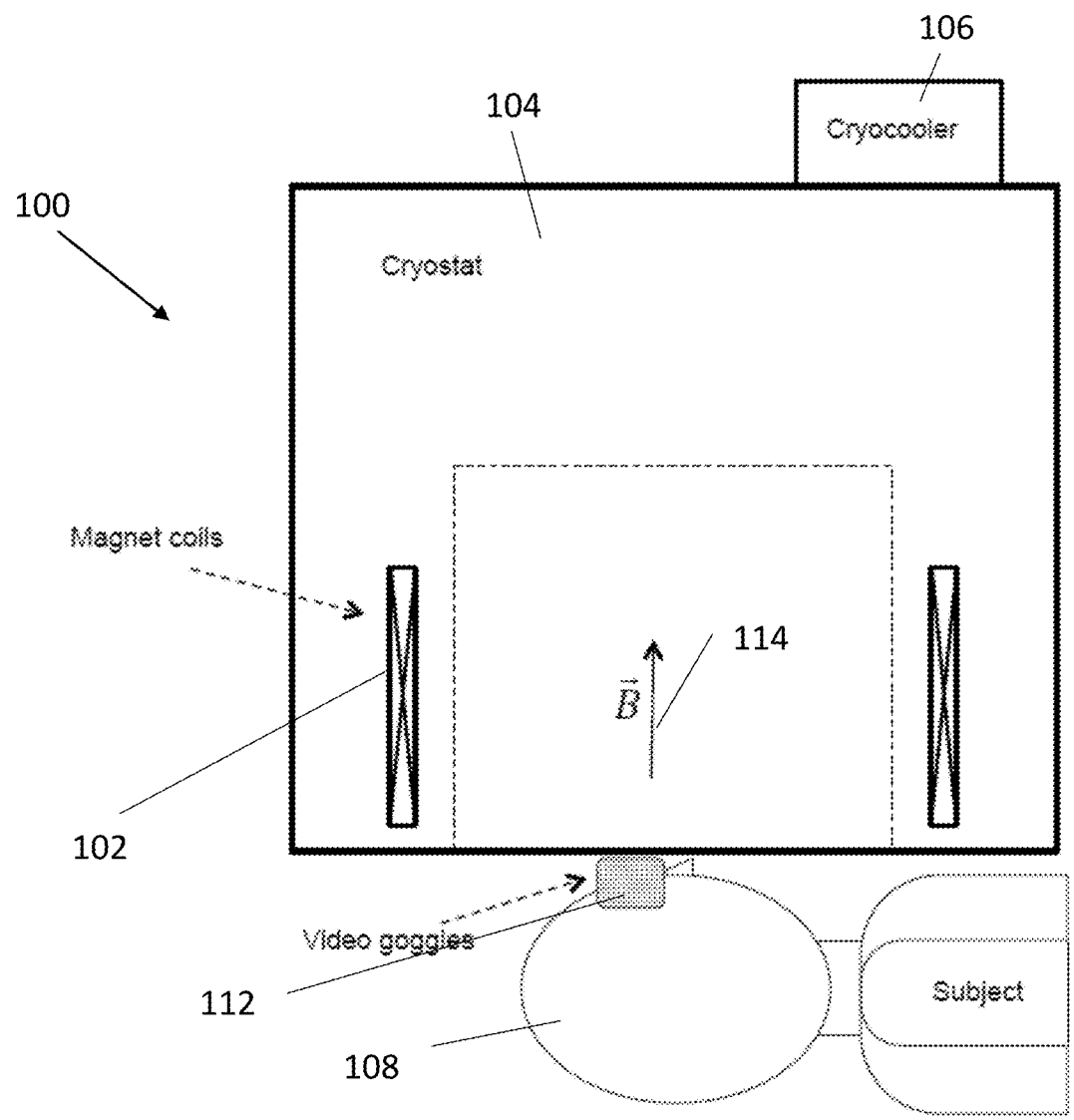
FIG. 2 illustrates a schematic diagram of a magnetic vestibular stimulation system, according to an embodiment of the present invention.

FIG. 2 illustrates a schematic diagram of a magnetic vestibular stimulation system, according to an embodiment of the present invention. The magnetic vestibular stimulation system 100 includes a magnet 102, as noted above, preferably, in some embodiments the magnet takes the form of a superconducting magnetic coil. The magnet 102 takes the form of a cylinder disposed in a cooling system. As illustrated in FIG. 2, the cooling system takes the form of a cryostat 104 and a cryocooler 106. However, any suitable cooling system known to or conceivable to one of skill in the art can also be used. Further, as illustrated in FIG. 2, the subject 108 is disposed beneath the cryostat 106. The subject 108 wears video goggles 112 in order to provide a virtual reality experience within the magnetic vestibular system. This virtual reality experience provides the subject 108 with the rehabilitation needed for the vestibular or balance disorder being treated or with a virtual reality experience for training, entertainment, or other application. FIG. 2 also illustrates the position of the subject 108 relative to the magnetic vestibular stimulation system 100. The subject 108 is positioned horizontal or perpendicular to a vertical axis of the cryostat 104. The magnetic field $\vec{B}$ 114 is oriented vertically, parallel to a vertical axis of the cryostat 104, such that the subject 108 and the magnetic field 114 are perpendicular to one another.

FIG. 3A illustrates a schematic diagram of a magnetic vestibular stimulation system, according to an embodiment of the present invention. The magnetic vestibular stimulation system 200 includes a magnet 202, as noted above, preferably, in some embodiments the magnet takes the form of a superconducting magnetic coil. The magnet 202 takes the form of a cylinder disposed in a cooling system. The cooling system, as illustrated in FIG. 3A, includes a cryostat 204 and also includes a cryocooler 206. However, any suitable cooling system known to or conceivable to one of skill in the art can also be used. Further, as illustrated in FIG. 3A, the subject 208 is disposed within a subject space 210 defined by the cryostat 204. The subject 208 wears video goggles 212 in order to provide a virtual reality experience within the magnetic vestibular system 200. This virtual reality experience provides the subject 208 with the rehabilitation needed for the vestibular or balance disorder being treated or with a virtual reality experience for training, entertainment, or other application. FIG. 3A also illustrates the position of the subject 208 within the subject space 210 of the magnetic vestibular stimulation system 200. The subject 208 is positioned horizontal or perpendicular to a horizontal axis of the cryostat 204. The subject's head is positioned within subject space 210. The magnetic field $\vec{B}$ 214 is oriented horizontally, parallel to a horizontal axis of the cryostat 204, such that the subject 208 and the magnetic field 214 are parallel to one another.

FIG. 3B illustrates a perspective view of a cylindrical cryostat and cryocooler for the magnetic vestibular stimulation system, according to an embodiment of the present invention. As illustrated in FIG. 3B the cryostat 204 takes the form of a cylinder. The cylinder of the cryostat 204 defines subject space 210, which as illustrated in FIG. 3B also takes the form of a cylinder. While cylindrical shapes are shown in FIGS. 3A and 3B, the cryostat 204 and subject space 210 can take any shape known to or conceivable to one of skill in the art. The cryostat 204 also includes a cryocooler 206. The cryostat 204 and cryocooler 206 can take any form known to or conceivable to one of skill in the art.

Figure 4:
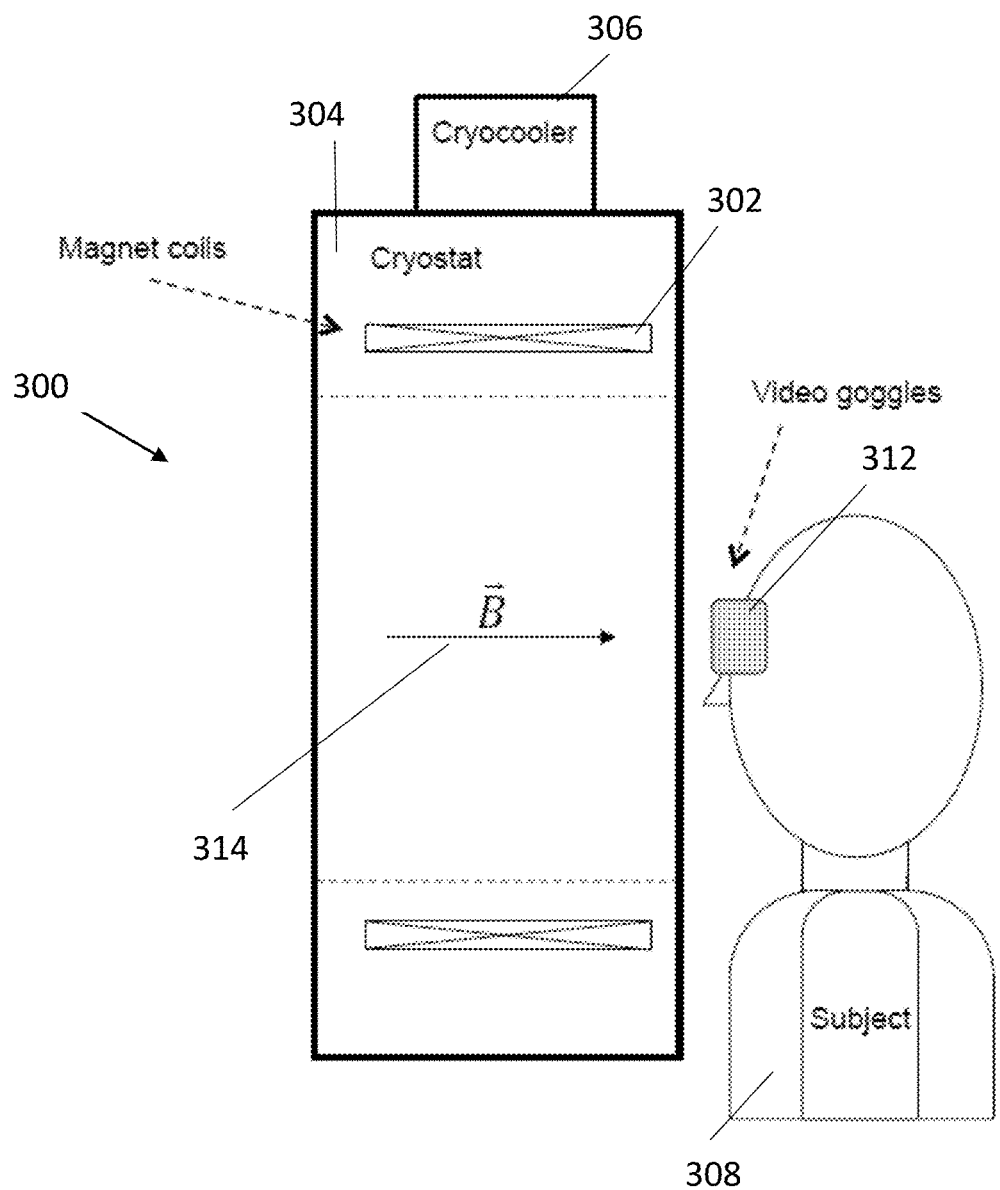
FIG. 4 illustrates a schematic diagram of a magnetic vestibular stimulation system, according to an embodiment of the present invention.

FIG. 4 illustrates a schematic diagram of a magnetic vestibular stimulation system, according to an embodiment of the present invention. The magnetic vestibular stimulation system 300 includes a magnet 302. The magnet 302 takes the form of a cylinder disposed in a cooling system. The cooling system as illustrated in FIG. 4 includes a cryostat 304 and also includes a cryocooler 306. However, any suitable cooling system known to or conceivable to one of skill in the art can also be used. Further, as illustrated in FIG. 4, the subject 308 is disposed in front of the cryostat 306. The subject 308 wears video goggles 312 in order to provide a virtual reality experience within the magnetic vestibular system. This virtual reality experience provides the subject 308 with the rehabilitation needed for the vestibular or balance disorder being treated or with a virtual reality experience for training, entertainment, or other application. FIG. 3 also illustrates the position of the subject 308 relative to the magnetic vestibular stimulation system 300. The subject 308 is positioned vertical or perpendicular to a horizontal axis of the cryostat 304. The magnetic field $\vec{B}$ 314 is oriented horizontally, parallel to a horizontal axis of the cryostat 304, such that the subject 308 and the magnetic field 314 are perpendicular to one another.

Figure 5:
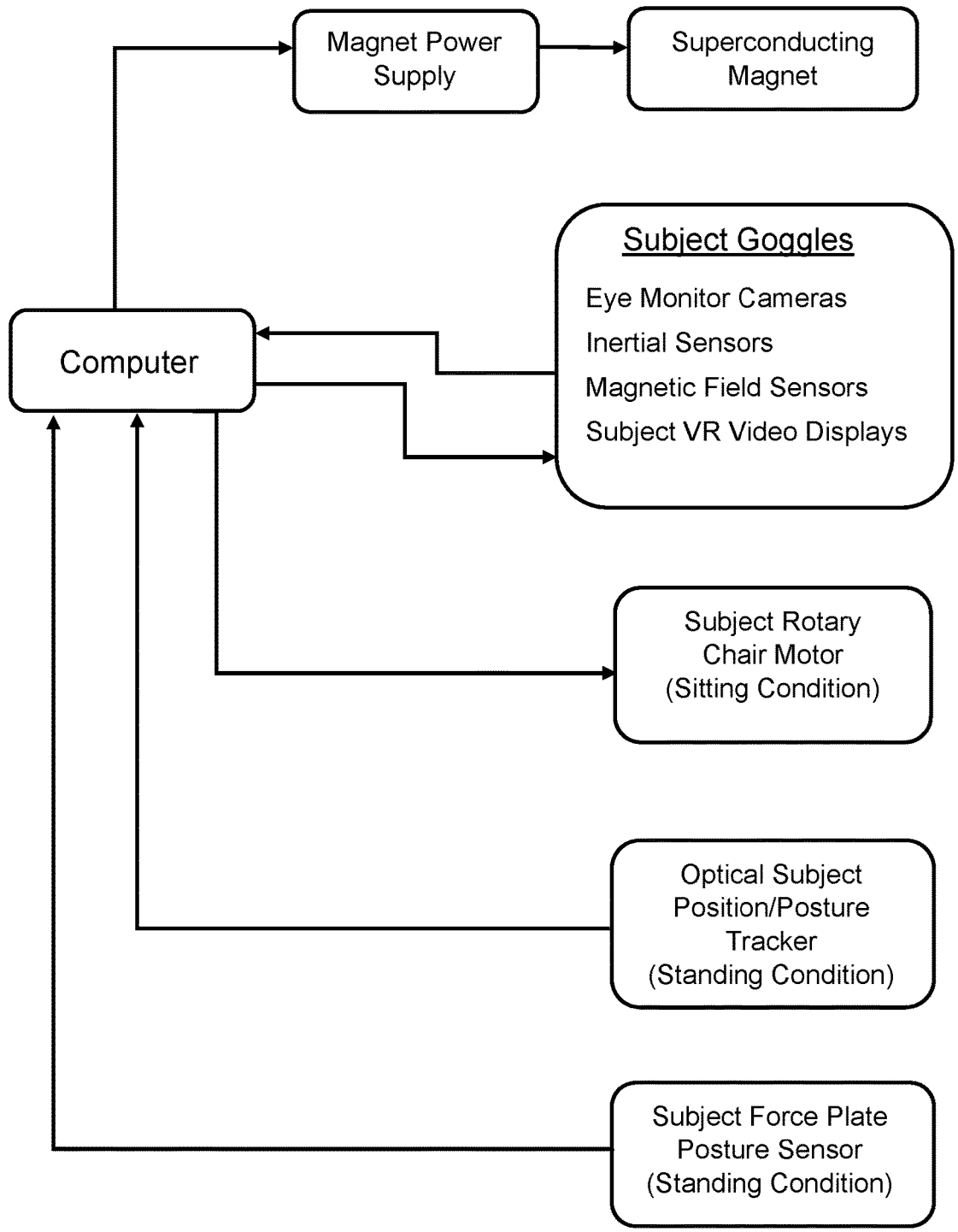
FIG. 5 illustrates a flow diagram for operation of a magnetic vestibular stimulation system, according to an embodiment of the present invention.

FIG. 5 illustrates a flow diagram for operation of a magnetic vestibular stimulation system, according to an embodiment of the present invention. As illustrated in FIG. 5 a computing device is used to control the magnet power supply and superconducting magnet. The computing device is also configured to receive and transmit information to and from the subject goggles, the subject rotary chair for instances where the subject is seated, the optical subject position/posture tracker for instances when the subject is standing, and a subject force plate posture sensor for when the subject is standing.

Figure 6:
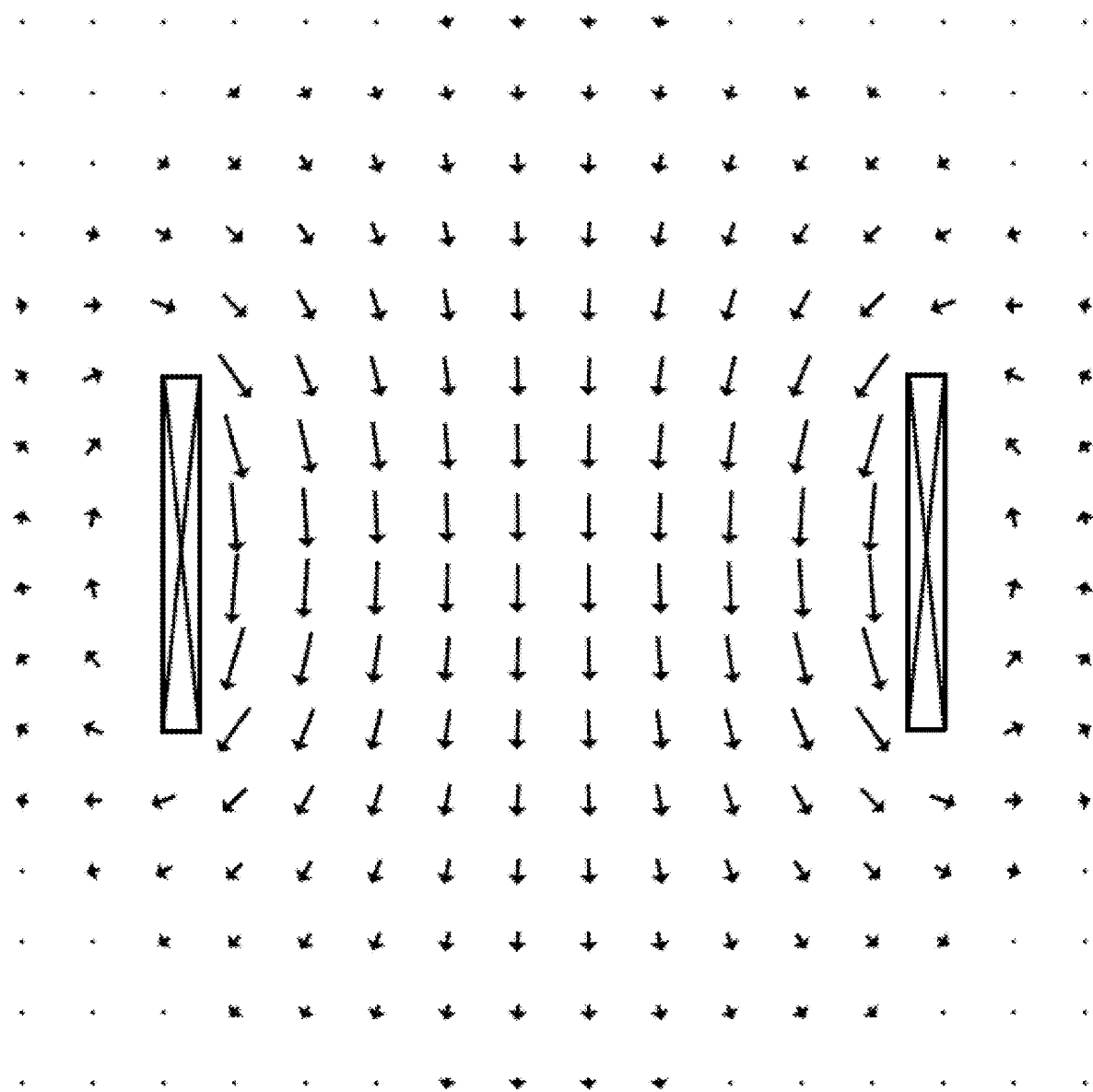
FIG. 6 illustrates a magnetic field associated with a magnet used according to an embodiment of the present invention.

FIG. 6 illustrates a magnetic field associated with a magnet used according to an embodiment of the present invention. As illustrated in FIG. 6 the magnet is configured to apply a magnetic field in the vestibular region of the user of the device. Preferably, the magnetic field generated by a magnet used according to the present invention is one that can be directed to the region of interest, and particularly to the vestibular region. It should be noted that a magnetic field appropriate for use with the present invention does not require the homogeneity necessary for many magnetic resonance imaging applications. The magnetic field of the present invention also does not require a radio-frequency (RF) component necessary for many magnetic resonance imaging applications. According to some embodiments of the present invention, the direction of the magnetic field of the magnet can also be changed. Alternately, given the configuration of the magnetic field of the present invention the user can also move his or her head relative to the magnetic field.

In some embodiments of the invention, the system can include two separate magnets with two orientations. A vertical magnet is included for the "subject upright" condition, and a horizontal magnet is included for "subject supine" condition. The system can also include the ability and structure to stimulate the vestibular system by rotating the subject about vertical axis while sitting. Subject posture can be measured while standing, using force plates and/or video position tracker. Other orientations of the system, magnets, subject, and magnetic field known to or conceivable to one of skill in the art could also be implemented.

In some embodiments, preferably a magnetic field strength of at least 7T is applied near the vestibular system. A weaker or stronger magnetic field can be used. It should be noted that the use of a 7T magnetic field is included only by way of example, and any other suitable strength of magnetic field known to or conceivable to one of skill in the art can also be used. Field homogeneity is not as critical as it is for MRI imaging. This gives more flexibility in magnet design. Magnetic field sensors near the ear will monitor the strength and direction of the magnetic field near the ears.

According to some aspects of the present invention, the goggles on subject's head include video cameras, to monitor movements of each eye, and an Inertial Measurement Unit (IMU) to measure head orientation to gravity. A magnetic field sensor is positioned near each ear, to measure the magnetic field strength and direction near the subject's vestibular system. It is important to know field strength and direction near each ear, to be correlated to resulting physiological response (the eye movement, balance, posture, sway, etc. measurements). This is especially important with a smaller magnet, because the magnetic field may not be homogeneous near the subject's ears. The magnetic field sensors are critical for feedback on magnetic field "dosage". The goggles include Virtual Reality (VR) video displays to present visual stimuli to subject. Goggles (and associated sensors and displays) are in wired or wireless communication with a computer for data transfer and potentially a power source. In other embodiments the goggles can be battery or directly powered.

A computing device is included to control magnetic field. The computing device connects to superconducting magnet power supply, so the magnetic field can be ramped up and down and reversed under computer control. The computing device is connected to the goggles. The computing device also receive video feed from the two eye cameras, receives IMU data stream, and receives magnetic field sensor signals from goggles. The computing device controls a Virtual Reality (VR) video presentation to small displays in subject goggles, to present visual stimulation to the subject. The computing device controls the rotary motor and provide rotational stimulus in conjunction with magnetic stimulation while subject is in sitting condition. The computing device receives force plate measurements. In standing condition, subject stands on force plates to measure subject's balance. The computing device is also configured to receive body posture and position information from a video tracker, to monitor posture and body sway.

It should be noted that any software associated with the present invention is programmed onto a non-transitory computer readable medium that can be read and executed by any of the computing devices mentioned in this application, such as smart watches, smart wearables, smart phones, tablets, phablets, laptop computers, personal computers, servers etc. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard, disk, reel-to-reel tape, cartridge tape, cassette tapes or cards, optical media such as CD-ROM, DVD, blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, or any other suitable data transmission means known to or conceivable by one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for magnetic stimulation of a vestibular system of a subject comprising:
    a cooling system;
    a magnet configured to generate a magnetic field directed to and configured for stimulation of the vestibular system; and
    goggles, wherein the goggles comprise video cameras to monitor movements of both eyes and wherein the goggles further comprise a magnetic field sensor.

2. The system of claim 1 wherein the magnetic field comprises a unidirectional magnetic field.

3. The system of claim 1 wherein the magnetic field comprises a multi-directional magnetic field.

4. The system of claim 1, wherein the magnet comprises a 7T magnet.

5. The system of claim 1 further comprising a computing device.

6. The system of claim 1 wherein the goggles further comprise a video display.

7. The system of claim 1 further comprising a device for tracking position and posture of the subject.

8. The system of claim 1 further comprising a superconducting magnet configured for vestibular stimulation.

9. The system of claim 1 wherein the cooling system comprises a cryostat and a cryocooler.

10. The system of claim 9 wherein the cryostat further comprises a subject space defined by a housing of the cryostat.

11. A method for magnetic stimulation of a vestibular system of a subject comprising:
    generating a magnetic field using a source of a magnetic field;
    cryocooling the source of the magnetic field;
    directing the magnetic field to the subject;
    stimulating the vestibular system of the subject using the magnetic field; and
    using goggles, wherein the goggles comprise video cameras to monitor movements of both eyes and wherein the goggles further comprise a magnetic field sensor.

12. The method of claim 11 wherein the magnetic field comprises a unidirectional magnetic field.

13. The method of claim 11 wherein the magnetic field comprises a multi-directional magnetic field.

14. The method of claim 11, further comprising using the magnetic field, wherein the source of the magnetic field comprises a 7T magnet.

15. The method of claim 11 further comprising using a computing device.

16. The method of claim 11 further comprising using the goggles, wherein said goggles comprise a video display.

* * * * *